(12) United States Patent
Goodson et al.

(10) Patent No.: US 11,834,416 B2
(45) Date of Patent: Dec. 5, 2023

(54) CLEAVABLE AGENTS

(71) Applicants: Board of Trustees of Southern Illinois University, Carbondale, IL (US); Vanderbilt University, Nashville, TN (US)

(72) Inventors: Boyd M. Goodson, Carbondale, IL (US); Eduard Y. Chekmenev, Troy, MI (US); Bryce E. Kidd, Carbondale, IL (US); Jamil A. Mashni, Carbondale, IL (US); Miranda Limbach, Creal Springs, IL (US); Yuqing Hou, Carbondale, IL (US); Fan Shi, Houston, TX (US)

(73) Assignees: Board of Trustees of Southern Illinois University, Carbondale, IL (US); Vanderbilt University, Nashville, TN (US)

( * ) Notice: Subject to any disclaimer, the term of this patent is extended or adjusted under 35 U.S.C. 154(b) by 33 days.

(21) Appl. No.: 16/698,332

(22) Filed: Nov. 27, 2019

(65) Prior Publication Data
US 2020/0172493 A1    Jun. 4, 2020

Related U.S. Application Data

(60) Provisional application No. 62/772,902, filed on Nov. 29, 2018.

(51) Int. Cl.
| | |
|---|---|
| *C07D 233/60* | (2006.01) |
| *G01R 33/28* | (2006.01) |
| *C07D 401/06* | (2006.01) |
| *C07D 241/12* | (2006.01) |
| *C07D 213/63* | (2006.01) |
| *C07F 9/6506* | (2006.01) |
| *B01J 31/12* | (2006.01) |
| *C07D 213/46* | (2006.01) |
| *G01R 33/46* | (2006.01) |

(52) U.S. Cl.
CPC ............ *C07D 233/60* (2013.01); *B01J 31/12* (2013.01); *C07D 213/46* (2013.01); *C07D 213/63* (2013.01); *C07D 241/12* (2013.01); *C07D 401/06* (2013.01); *C07F 9/6506* (2013.01); *G01R 33/282* (2013.01); *B01J 2531/827* (2013.01); *G01R 33/46* (2013.01)

(58) Field of Classification Search
CPC .................................................. C07D 233/60
See application file for complete search history.

(56) References Cited

U.S. PATENT DOCUMENTS

| | | |
|---|---|---|
| 8,154,284 B2 | 4/2012 | Duckett et al. |
| 8,766,631 B2 | 7/2014 | Hofmann et al. |
| 8,825,132 B2 | 9/2014 | Lohman et al. |
| 9,707,550 B2 | 7/2017 | Goodson et al. |
| 9,790,245 B2 | 10/2017 | Chekmenev et al. |
| 2016/0169998 A1 | 6/2016 | Warren et al. |
| 2016/0263256 A1 | 9/2016 | Aime et al. |

FOREIGN PATENT DOCUMENTS

| | | |
|---|---|---|
| EP | 2374016 B1 | 5/2017 |
| WO | 2017002113 A1 | 1/2017 |
| WO | 2018162895 A2 | 9/2018 |
| WO | 2018209334 A1 | 11/2018 |
| WO | 2019008308 A1 | 1/2019 |
| WO | 2019020989 A2 | 1/2019 |
| WO | 2019209344 A1 | 10/2019 |

OTHER PUBLICATIONS

Kidd et al. (Chem. Eur.J. 2018, 24, 10641-10645).*
Adams RW et al., Reversible Interactions with Para-Hydrogen Enhance NMR Sensitivity by Polarization Transfer, Science, 2009, pp. 1708-1711, vol. 323, No. 5922.
Ardenkjaer-Larsen JH et al., Increase in Signal-to-Noise Ratio of > 10,000 Times in Liquid-State NMR, Proceedings of the National Academy of Sciences of the United States of America, 2003, pp. 10158-10163, vol. 100, No. 18.
Barskiy DA et al., Over 20% 15N Hyperpolarization in Under One Minute for Metronidazole, an Antibiotic and Hypoxia Probe, Journal of the American Chemical Society, 2016, pp. 8080-8083, vol. 138, No. 26.
Bastiaansen Jam et al., In Vivo Enzymatic Activity of AcetylCoA Synthetase in Skeletal Muscle Revealed by 13C Turnover from Hyperpolarized [1-13C]Acetate to [1-13C]Acetylcarnitine, Biochimica et Biophysica Acta, 2013, pp. 4171-4178, vol. 1830, No. 8.
Bowers CR and Weitekamp DP, Transformation of Symmetrization Order to Nuclear-Spin Magnetization by Chemical Reaction and Nuclear Magnetic Resonance, Physical Review Letters, 1986, pp. 2645-2648, vol. 57, No. 21.
Bowers CR and Weitekamp DP, Parahydrogen and Synthesis Allow Dramatically Enhanced Nuclear Alignment, Journal of the American Chemical Society, 1987, pp. 5541-5542, vol. 109, No. 18.
Colell JFP et al., Direct Hyperpolarization of Nitrogen-15 in Aqueous Media with Parahydrogen in Reversible Exchange, Journal of the American Chemical Society, 2017, pp. 7761-7767, vol. 139, No. 23.
Cowley MJ et al., Iridium N-Heterocyclic Carbene Complexes as Efficient Catalysts for Magnetization Transfer from Para-Hydrogen, Journal of the American Chemical Society, 2011, pp. 6134-6137, vol. 133, No. 16.
Duckett SB and Mewis RE, Application of Parahydrogen Induced Polarization Techniques in NMR Spectroscopy and Imaging, Accounts of Chemical Research, 2012, pp. 1247-1257, vol. 45, No. 8.

(Continued)

*Primary Examiner* — Brian E McDowell
(74) *Attorney, Agent, or Firm* — Stinson LLP

(57) ABSTRACT

The present disclosure is directed to a cleavable agent for enhanced magnetic resonance generally corresponding to the formula Y-L-R, wherein Y represents a catalyst-binding moiety having at least one isotopically labeled heteroatom, L represents a cleavable bond, and R represents a hyperpolarized payload having at least one isotopically labeled carbon. Also disclosed herein is a method of cleaving the cleavable agent for enhanced magnetic resonance.

1 Claim, 7 Drawing Sheets

(56) References Cited

OTHER PUBLICATIONS

Eisenschmid TC et al., Para Hydrogen Induced Polarization in Hydrogenation Reactions, Journal of the American Chemical Society, 1987, pp. 8089-8091, vol. 109, No. 26.
Eshuis N et al., Toward Nanomolar Detection by NMR through SABRE Hyperpolarization, Journal of the American Chemical Society, 2014, pp. 2695-2698, vol. 136, No. 7.
Fekete M et al., Iridium(III) Hydrido N-Heterocyclic Carbene-Phosphine Complexes as Catalysts in Magnetization Transfer Reactions, Inorganic Chemistry, 2013, p. 13453-13461, vol. 52, No. 23.
Gallagher FA et al., Magnetic Resonance Imaging of pH In Vivo Using Hyperpolarized 13C-Labelled Bicarbonate, Nature, 2008, pp. 940-943, vol. 453, No. 7197.
Hovener J-B et al., Parahydrogen-Based Hyperpolarization for Biomedicine, Angewandte Chemie International Edition, 2018, p. 11140-11162, vol. 57, No. 35.
Iali W et al., Achieving High Levels of NMR-Hyperpolarization in Aqueous Media with Minimal Catalyst Contamination Using SABRE, Chemistry A European Journal, 2017, p. 10491-10495, vol. 23, No. 44.
Iali W et al., Using Parahydrogen to Hyperpolarize Amines, Amides, Carboxylic Acids, Alcohols, Phosphates, and Carbonates, Science Advances, 2018, page eaao6250, vol. 4, No. 1.
Kidd BE et al., Toward Cleavable Metabolic/pH Sensing "Double Agents" Hyperpolarized by NMR Signal Amplification by Reversible Exchange, Chemistry A European Journal, 2018, p. 10641-10645, vol. 24, No. 42.
Kovtunov KV et al., Heterogeneous Microtesla SABRE Enhancement of 15N Nmr Signals, Angewandte Chemie International Edition, 2017, p. 10433-10437, vol. 56, No. 35.
Kovtunov KV et al., Imaging of Biomolecular NMR Signals Amplified by Reversible Exchange with Parahydrogen Inside an MRI Scanner, The Journal of Physical Chemistry C, 2017, p. 25994-25999, vol. 121, No. 46.
Kurhanewicz J et al., Analysis of Cancer Metabolism by Imaging Hyperpolarized Nuclei: Prospects for Translation to Clinical Research, Neoplasia, 2011, pp. 81-97, vol. 13, No. 2.
Licha K et al., New Contrast Agents for Optical Imaging: Acid-Cleavable Conjugates of Cyanine Dyes with Biomolecules, Proceedings SPIE vol. 3600, Biomedical Imaging: Reporters, Dyes, and Instrumentation, 1999, accessible at https://doi.org/10.1117/12.351013 (abstract only).
Mashimo T et al., Acetate Is a Bioenergetic Substrate for Human Glioblastoma and Brain Metastases, Cell, 2014, pp. 1603-1614, vol. 159, No. 7.
Mashni J et al., Toward Cleavable Metabolic/pH Sensing "Double Agents" Hyperpolarized via NMR Signal Amplification by Reversible Exchange, abstract presented at the 59th Experimental Nuclear Magnetic Resonance Conference, Apr. 29 - May 4, 2018, Orlando, Florida, available at http://www.enc-conference.org/portals/0/Abstracts2018/ENC20188054.1456VER.1.pdf.
Mewis RE et al., Deactivation of Signal Amplification by Reversible Exchange Catalysis, Progress Towards In Vivo Application, Chemical Communications, 2015, pp. 9857-9859, vol. 51, No. 48.
Mishkovsky M et al., In Vivo Detection of Brain Krebs Cycle Intermediate by Hyperpolarized Magnetic Resonance, Journal of Cerebral Blood Flow & Metabolism, 2012, pp. 2108-2113, vol. 32, No. 12.
Natterer J and Bargon J, Parahydrogen Induced Polarization, Progress in Nuclear Magnetic Resonance Spectroscopy, 1997, pp. 293-315, vol. 31, No. 4.
Nelson SJ et al., Metabolic Imaging of Patients with Prostate Cancer Using Hyperpolarized [1-13C]Pyruvate, Science Translational Medicine, 2013, p. 198ra108, vol. 5, No. 198.
Nikolaou P et al., NMR Hyperpolarization Techniques for Biomedicine, Chemistry A European Journal, 2015, pp. 3156-3166, vol. 21, No. 8.
Reineri F et al., Use of Labile Precursors for the Generation of Hyperpolarized Molecules from Hydrogenation with Parahydrogen and Aqueous-Phase Extraction, Angewandte Chemie International Edition, 2011, pp. 7350-7353, vol. 50, No. 32.
Reineri F et al., ParaHydrogen Induced Polarization of 13C Carboxylate Resonance in Acetate and Pyruvate, Nature Communications, 2015, article No. 5858, vol. 6.
Shchepin RV et al., Hyperpolarization of "Neat" Liquids by NMR Signal Amplification by Reversible Exchange, The Journal of Physical Chemistry Letters, 2015, pp. 1961-1967, vol. 6, No. 10.
Shchepin RV et al., 15N Hyperpolarization of Imidazole-15N2 for Magnetic Resonance pH Sensing via Sabre- Sheath, Acs Sensors, 2016, pp. 640-644, vol. 1, No. 6.
Shchepin RV et al., Efficient Synthesis of Molecular Precursors for Para-Hydrogen-Induced Polarization of Ethyl Acetate-1-13C and Beyond, Angewandte Chemie International Edition, 2016, pp. 6071-6074, vol. 55, No. 20.
Shchepin RV et al., NMR Signal Amplification by Reversible Exchange of Sulfur-Heterocyclic Compounds Found in Petroleum, ChemistrySelect, 2016, pp. 2552-2555, vol. 1, No. 10.
Shchepin RV et al., Toward Hyperpolarized 19F Molecular Imaging via Reversible Exchange with Parahydrogen, ChemPhysChem, 2017, pp. 1961-1965, vol. 18, No. 15.
Shchepin RV et al., Spin Relays Enable Efficient Long-Range Heteronuclear Signal Amplification by Reversible Exchange, The Journal of Physical Chemistry C, 2017, p. 28425-48434, vol. 121, No. 51.
Shchepin RV et al., Spin-Lattice Relaxation of Hyperpolarized Metronidazole in Signal Amplification by Reversible Exchange in Micro-Tesla Fields, The Journal of Physical Chemistry C, 2018, pp. 4984-4996, vol. 122, No. 9.
Shi F et al., Heterogeneous Solution NMR Signal Amplification by Reversible Exchange, Angewandte Chemie International Edition, 2014, pp. 7495-7498, vol. 53, No. 29.
Shi F et al., Nanoscale Catalysts for NMR Signal Enhancement by Reversible Exchange, The Journal of Physical Chemistry C, 2015, pp. 7525-7533, vol. 119, No. 13.
Shi F et al., Aqueous NMR Signal Enhancement by Reversible Exchange in a Single Step Using Water-Soluble Catalysts, The Journal of Physical Chemistry C, 2016, p. 12149-12156, vol. 120, No. 22.
Spannring P et al., A New Ir-NHC Catalyst for Signal Amplification by Reversible Exchange in D20, Chemistry A European Journal, 2016, pp. 9277-9282, vol. 22, No. 27.
Theis T et al., Microtesla SABRE Enables 10% Nitrogen-15 Nuclear Spin Polarization, Journal of the American Chemical Society, 2015, pp. 1404-1407, vol. 137, No. 4.
Theis T et al., Direct and Cost-Efficient Hyperpolarization of Long-Lived Nuclear Spin States on Universal 15N2- Diazirine Molecular Tags, Science Advances, 2016, page e1501438, vol. 2, No. 3.
Truong ML et al., Irreversible Catalyst Activation Enables Hyperpolarization and Water Solubility for NMR Signal Amplification by Reversible Exchange, The Journal of Physical Chemistry B, 2014, p. 13882-13889, vol. 118, No. 48.
Truong ML et al., 15N Hyperpolarization by Reversible Exchange Using SABRE-SHEATH, The Journal of Physical Chemistry C, 2015, pp. 8786-8797, vol. 119, No. 16.
Vazquez-Serrano LD et al., The Search for New Hydrogenation Catalyst Motifs Based on N-Heterocyclic Carbene Ligands, Inorganica Chimica Acta, 2006, pp. 2786-2797, vol. 359, No. 9.
Weissleder R., Molecular Imaging in Cancer, Science, 2006, pp. 1168-1171, vol. 312, No. 5777.

* cited by examiner

CLEAVABLE AGENTS

CROSS-REFERENCE TO RELATED APPLICATION

This application claims the benefit of U.S. Provisional Patent Application Ser. No. 62/772,902, filed Nov. 29, 2018, the entire content of which is herein incorporated by reference.

STATEMENT REGARDING FEDERALLY SPONSORED RESEARCH OR DEVELOPMENT

This invention was made with government support under Grant Nos. CHE-1416268 and CHE-1416432 awarded by the National Science Foundation; Grant Nos. EB020323 and CA220137 awarded by the National Institutes of Health; and Grant Nos. W81XWH-12-1-0159, W81XWH-15-1-0271, and W81X-WH-15-1-0272 awarded by the Department of Defense. The government has certain rights in the invention.

FIELD OF THE DISCLOSURE

The present invention relates generally to cleavable agents and methods of cleaving the cleavable agents.

BACKGROUND OF THE DISCLOSURE

The ability of magnetic resonance to spectrally discriminate among different biochemical states makes MRI an attractive modality for molecular imaging; however, low detection sensitivity generally relegates conventional MRI to imaging high-concentration species such as water in the body, which is ~80 M in $^1$H spins. Hyperpolarization can combat this problem by generating highly non-equilibrium nuclear spin population distributions, thereby providing orders-of-magnitude improvements in MR detection sensitivity for select substances.

One relatively new type of hyperpolarization is SABRE, introduced by Duckett, Green, and co-workers at the University of York. SABRE uses a catalyst to co-locate para-hydrogen (para-$H_2$)—a cheap and easy-to-produce source of nuclear spin order—and a target substrate within a transient complex, allowing spin order to transfer to substrate spins via scalar couplings, generally within a properly matched applied field. SABRE is rapid (working in seconds), cheap, scalable, and relatively easy to perform, without the requirement for major specialized instrumentation. A drawback of SABRE to date has been the limited types of amenable substrates. Because of the need to transiently and reversibly bind to the SABRE catalyst, which is usually an iridium-based organometallic complex, most substrates that can undergo direct polarization transfer via SABRE have an $sp^1$ or $sp^2$-hybridized N or S atom with a lone pair. This limitation currently precludes direct hyperpolarization of countless molecules that could be targets for any number of applications.

One key example of desirable targets is the family of carboxylic acid derivatives that participate in key cycles of cellular metabolism. Such agents are of particular interest because their down-stream metabolic products, such as Kreb cycle intermediates, can serve as biomarkers of variant physiological states or disease (manifested, for example, by altered relative production rates of metabolites). For example, hyperpolarized (HP)$^{13}$C-pyruvate can enable metabolic imaging of various pathological conditions, highlighted by recent clinical trials for prostate cancer; pH imaging using HP $^{13}$C-carbonate has also been demonstrated. Acetate is rapidly taken up by the brain and undergoes differential metabolism in glioblastoma multiforme, an aggressive brain cancer; correspondingly $^{13}$C-acetate is of interest and has been demonstrated in hyperpolarized form.

More generally, a growing number of small-molecule targets can be envisioned that exploit some biochemical effect, be it differential cellular uptake, differential metabolism, or other sensing of different physiological or pathological states or environments. However, a large majority are poorly amenable to direct and efficient hyperpolarization via SABRE.

SUMMARY OF THE DISCLOSURE

This disclosure describes a new class of substrate molecules amenable to SABRE hyperpolarization. These molecules are designed to undergo reversible binding to SABRE catalysts and become hyperpolarized rapidly by para-$H_2$, such that more than one part of the agent becomes hyperpolarized. Moreover, upon bond cleavage (performed at will), different agents are rapidly generated with different sensing properties in a manner that maintains the hyperpolarized state. This invention provides a general approach for rapidly and cheaply creating a wide range of hyperpolarized substrates via SABRE. Furthermore, one can imagine combining this method with heterogeneous catalysts and/or catalyst extraction methods to generate pure HP species, as well as SABRE in aqueous environments or with auxiliary ligands to modulate substrate/catalyst interactions. Moreover, a variety of catalyst-binding moieties and imaging payloads-connected by bonding that may be cleaved or otherwise activated by exogenous or endogenous mechanisms—are readily envisioned, opening a door to the rapid and inexpensive generation of long-lived HP states within a wide range of agents for in vivo molecular imaging, as well as other applications in magnetic resonance. The described agents thus helps pave the way to the biomedical translation of this hyperpolarization method with unprecedented advantages of speed and cost.

The present disclosure relates to a cleavable agent corresponding in structure to the formula:

Y-L-R wherein Y is a catalyst-binding moiety, L is a cleavable bond, and R is a hyperpolarized payload; wherein Y contains at least one isotopically labeled heteroatom and R contains at least one isotopically labeled carbon.

Also provided herein are methods of cleaving the cleavable agent of the present disclosure for enhanced magnetic resonance, the methods comprising: hyperpolarizing the cleavable agent via SABRE within a magnetic shield; and depressurizing a container containing the hyperpolarized cleavable agent to cause rapid hydrolytic, aminolytic, or enzymatic cleavage of the bond between the heterocyclic moiety and the carboxylic acid or carboxylic acid precursor moiety.

Other objects and features will be in part apparent and in part pointed out hereinafter.

DESCRIPTION OF THE DRAWINGS

Corresponding reference characters indicate corresponding parts throughout the drawings.

DETAILED DESCRIPTION OF THE DISCLOSURE

Figure 1:
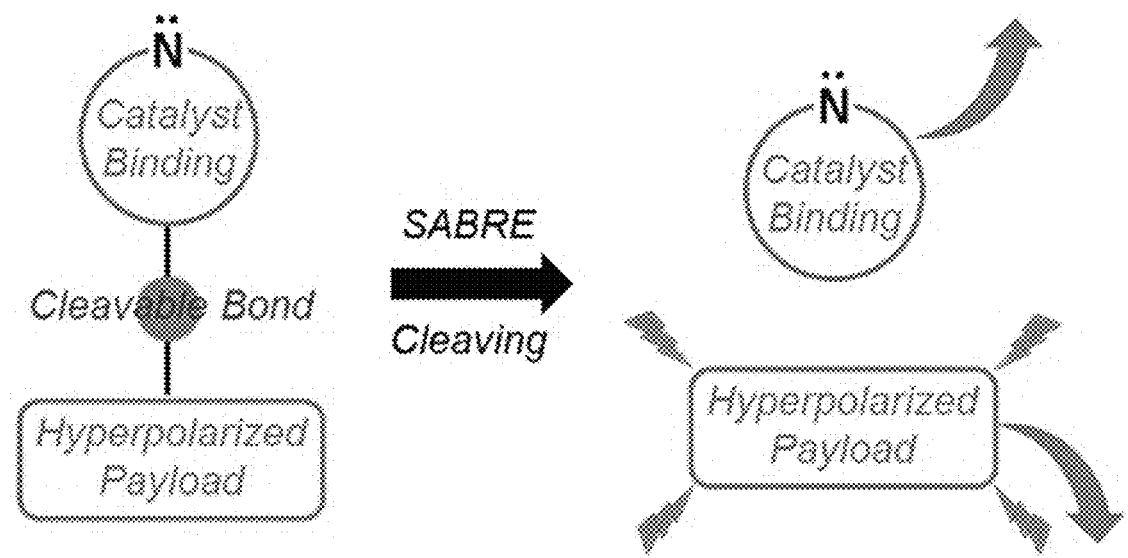
FIG. 1 is a scheme of cleavable SABRE agents.

The present invention is related to cleavable agents having the general formula:

Y-L-R wherein Y the catalyst binding moiety, L is a cleavable bond, and R is a hyperpolarized payload. In various embodiments, Y can include an isotopically labeled heteroatom, such as an isotopically labeled nitrogen (e.g., $^{15}N$), and/or R can include an isotopically labeled carbon (e.g., $^{13}C$). For example, in one embodiment, Y includes an isotopically labeled nitrogen ($^{15}N$) and R is not isotopically labeled. In another embodiment, Y is not isotopically labeled and R includes an isotopically labeled carbon ($^{13}C$). In an alternative embodiment, Y includes an isotopically labeled nitrogen ($^{15}N$) and R includes an isotopically labeled carbon ($^{13}C$). The cleaving of a cleavable agent according to this structure is depicted in FIG. 1. As explained below, payload hyperpolarization is achieved, for example, via SABRE-SHEATH through the spin-relay network, followed by cleavage.

In various embodiments, the hyperpolarized payload can comprise any payload class known in the art, such as, for example, carboxylic acids and carboxylates (particularly those involved in metabolic cycles, such as the citric acid cycle), urea, amino acids (such as alanine, glutamine, arginine, etc.), molecules involved in lipid metabolism (such as choline and derivatives thereof), neurotransmitters, sugars (such as glucose, fructose, etc.), nucleic acids, drugs, metabolites, and/or other molecules that might bind to or be substrates of enzymes or other proteins or biomacromolecules. Preferably, the hyperpolarized payload comprises a carboxylic acid, carboxylate, or amino acid. For example, the hyperpolarized payload comprises a carboxylic acid or carboxylate thereof. In various embodiments, the hyperpolarized payload comprises an amino acid.

In the above structure, Y binds to a SABRE catalyst. The skilled person will be able to select suitable SABRE catalysts for use with the present invention. Generally, iridium-type catalysts are used, such as, for example, [Ir-IMes; [IrCl(COD)(IMes)], (IMes=1,3-bis(2,4,6-trimethylphenyl), imidazole-2-ylidene; COD=cyclooctadiene)]. This catalyst can be activated by addition of a hydrogen present in the substrate, which causes oxidation of the iridium (to $Ir^{3+}$) and the catalyst becomes hexacoordinate (following hydrogenation and loss of the COD group and chloride ion). Iridium catalysts useful in the present invention are generally defined by the NHC (N-heterocyclic carbene) group, e.g., the "IMes" group. As another example, the NHC group can be hydrogenated so that the double bond of the 5-membered ring is hydrogenated to make a "SIMes" group. Alternatively or additionally, the NHC can have different rings, can be functionalized to alter the electronic or steric properties (such as those affecting catalytic activity), and can be functionalized to alter the solubility of the catalyst (such as to make it more water-soluble). The ligand site opposite the NHC group is generally not exchangeable and may be used to tether the catalysts to a support (to make microscale or nanoscale heterogeneous catalysts). However, the NHC group can also be functionalized with known chemistries to tether the catalyst to supports instead of the opposing ligand site.

A number of specific catalyst-binding moieties are amendable to the present disclosure. Two examples of particular embodiments of catalyst-binding moieties include: (A) those using 6-membered nitrogen heterocycles (e.g., pyridine-based rings); and (B) those using 5-membered nitrogen heterocycles (e.g., imidazole-based rings). Structural variants of carboxylic acids can be used, such that activation or cleavage of the bonding moiety results in the production of a carboxylic acid or its corresponding salt. As described above, isotopic labeling with $^{15}N$ and $^{13}C$ in the cleavable agents can be used.

In various embodiments, the cleavable agent can correspond in structure to Formula I, Formula II, Formula III, Formula IV, Formula V, Formula VI, Formula VII, Formula VIII, or Formula IX:

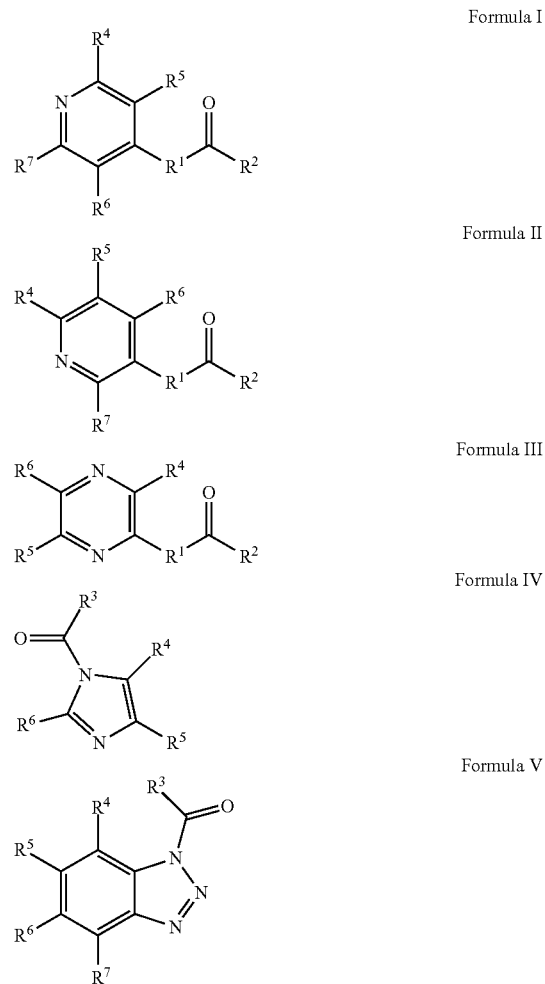

-continued

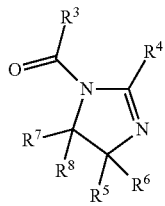
Formula VI

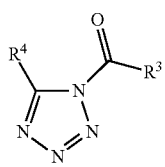
Formula VII

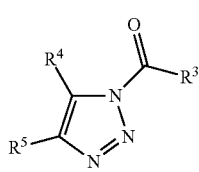
Formula VIII

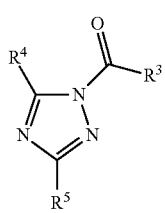
Formula IX wherein:
R¹ is a bond or optionally substituted alkylene;
R² is alkylene carboxylate or optionally substituted alkyl;
R³ is optionally substituted alkyl, alkenyl, heteroaryl, haloalkyl, guanidine, alkylene carboxylate, alkenylene carboxylate, or R³ corresponds in structure to:

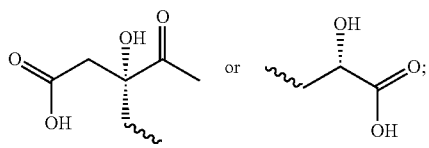

and
R⁴, R⁵, R⁶, R⁷, and R⁸ are independently selected from the group consisting of hydrogen, alkyl, alkenyl, heteroaryl, haloalkyl, guanidine alkylene carboxylate, and alkenylene carboxylate, each of which may be optionally substituted.

For example, R¹ can be an alkylene having from one to three carbon atoms, for example, methylene. Alternatively, R¹ is a bond. R² can be optionally methyl or C(O)OH. R³ can be, for example, methyl, ethenyl, pyridyl, CF₃, guanidine, or acrylic carboxylate.

In the above formulas, at least one nitrogen can be isotopically labeled, e.g., by $^{15}N$, and/or at least one carbon on one or more of R¹, R², and R³ can be isotopically labeled, e.g., by $^{13}C$. For example, the cleavable agent can include at least one isotopically labeled nitrogen ($^{15}N$), such as one, two, three, or four isotopically labeled nitrogen atoms ($^{15}N$), the maximum number of which is dependent on how many nitrogen atoms are included in the heteroaryl ring. Similarly, the cleavable agent can include at least one isotopically labeled carbon ($^{13}C$), such as one, two, three, four, etc. labeled carbon atoms ($^{13}C$), the maximum number of which is dependent on the sum of the number of carbon atoms included in substituents R¹, R², and R³.

As an example, in one embodiment, at least one nitrogen atom is isotopically labeled ($^{15}N$) and no carbon atom is isotopically labeled. In an alternative embodiment, at least one carbon atom is isotopically labeled ($^{13}C$) and no nitrogen atom is isotopically labeled. In a further embodiment, at least one nitrogen atom is isotopically labeled ($^{15}N$) and at least one carbon atom is isotopically labeled ($^{13}C$).

Particular examples of compounds according to these structures include:

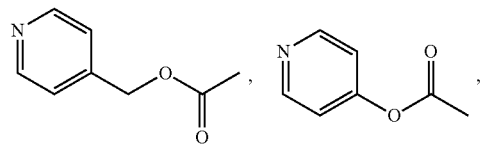

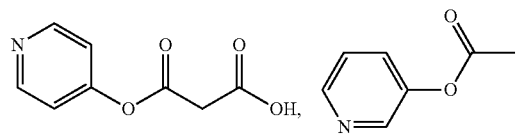

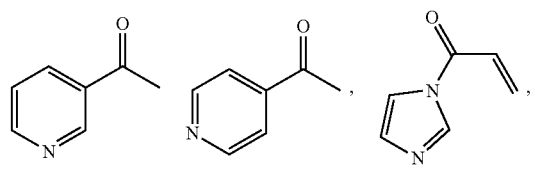

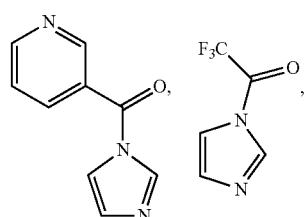

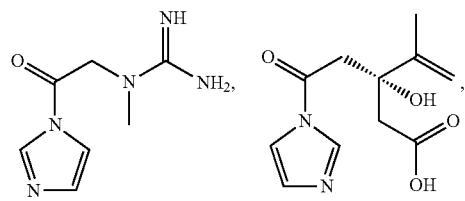

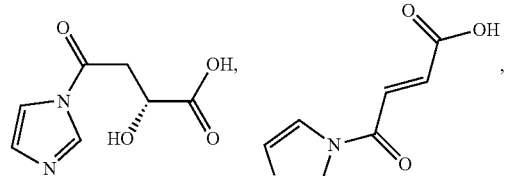

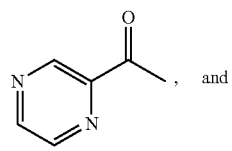, and

-continued

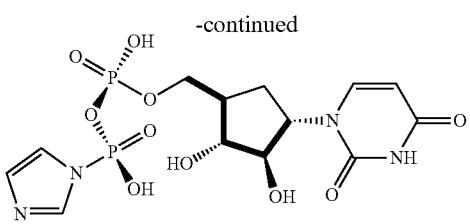

In various embodiments, at least one nitrogen on the above-depicted compounds is isotopically labeled, e.g., by $^{15}N$, and/or at least one carbon on the acyclic chain is isotopically labeled, e.g., by $^{13}C$.

Method of Synthesizing the Cleavable Agents

A method of synthesizing the cleavable agents of the present disclosure is also described herein. In general, the method requires reacting a carboxylic acid containing the $R^2$ or $R^1$ group, e.g.:

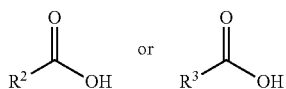

with a halo(alkoxy)alkyl in order to provide a carbonyl halide containing the $R^2$ or $R^3$ group, e.g.:

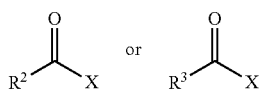

wherein X is a halide (fluorine, chlorine, bromine, or iodine). X is preferably chlorine. In the halo(alkoxy)alkyl, the halo can comprise fluorine, chlorine, bromine, or iodine, and the alkyl can be substituted one, two, three, four, etc. times with halo, the maximum number of which is dependent on the number of available substitution locations on the alkyl group. The alkyl and alkoxy group can independently contain, for example, from 1 to 18 carbon atoms, preferably from 1 to 12 carbon atoms, and more preferably, from 1 to 6 carbon atoms. For example, in some embodiments, halo(alkoxyl)alkyl can comprise dichloro(methoxy)methane. This reaction may be subjected to heating as necessary and can be performed under an inert atmosphere (e.g., an argon atmosphere) for a period of time. For example, the reaction can be performed at or around room temperature, about 30° C., about 40° C., about 50° C., about 60° C., about 70° C., about 80° C., about 90° C., about 100° C., or higher. As an example, the reaction can be performed at about room temperature to about 100° C., at about room temperature to about 80° C., about room temperature to about 60° C., at about room temperature to about 50° C., at about room temperature to about 40° C., or at about room temperature to about 30° C. It will be understood to the skilled person that "room temperature" generally designates a temperature of from about 20 to about 25° C. The reaction can proceed for about 30 minutes to about 2 hours, for example from about 30 minutes to about 90 minutes, or from about 30 minutes to about 60 minutes, as necessary to complete the reaction. Preferably, the reaction takes place in less than two hours.

The carbonyl halide is then reacted with the desired nitrogen-containing heteroaryl group, optionally in a solvent, to provide a cleavable agent as described in detail above. Any suitable solvent known in the art can be used, for example, dichloromethane, triethylamine, acetone, chloroform, cyclohexane, dimethylformamide, toluene, tetrahydrofuran, ethanol, xylene, or a combination thereof. The reaction may be performed at room temperature or can be cooled. The reaction can also be performed under an inert atmosphere (e.g., an argon atmosphere) for a period of time. For example, the reaction can proceed at or around room temperature or can be cooled to about 10° C., about 0° C., about –10° C., or about –20° C. As an example, the reaction can be performed from about 10° C. to about room temperature, from about 0° C. to about room temperature, from about –10° C. to about room temperature, or from about –20° C. to about room temperature. The reaction can proceed for about 1 hour to about 24 hours, for example from about 1 hour to about 18 hours, from about 1 hour to about 12 hours, from about 1 hour to about 6 hours, or from about 1 hour to about 2 hours, as necessary to complete the reaction. Preferably, the reaction takes place in about 24 hours or less.

Method of Hyperpolarizing the Cleavable Agents

Also provided herein is a method of hyperpolarizing the cleavable agents. The methods of the present disclosure use milliTesla and/or microTesla fields.

Figure 9:
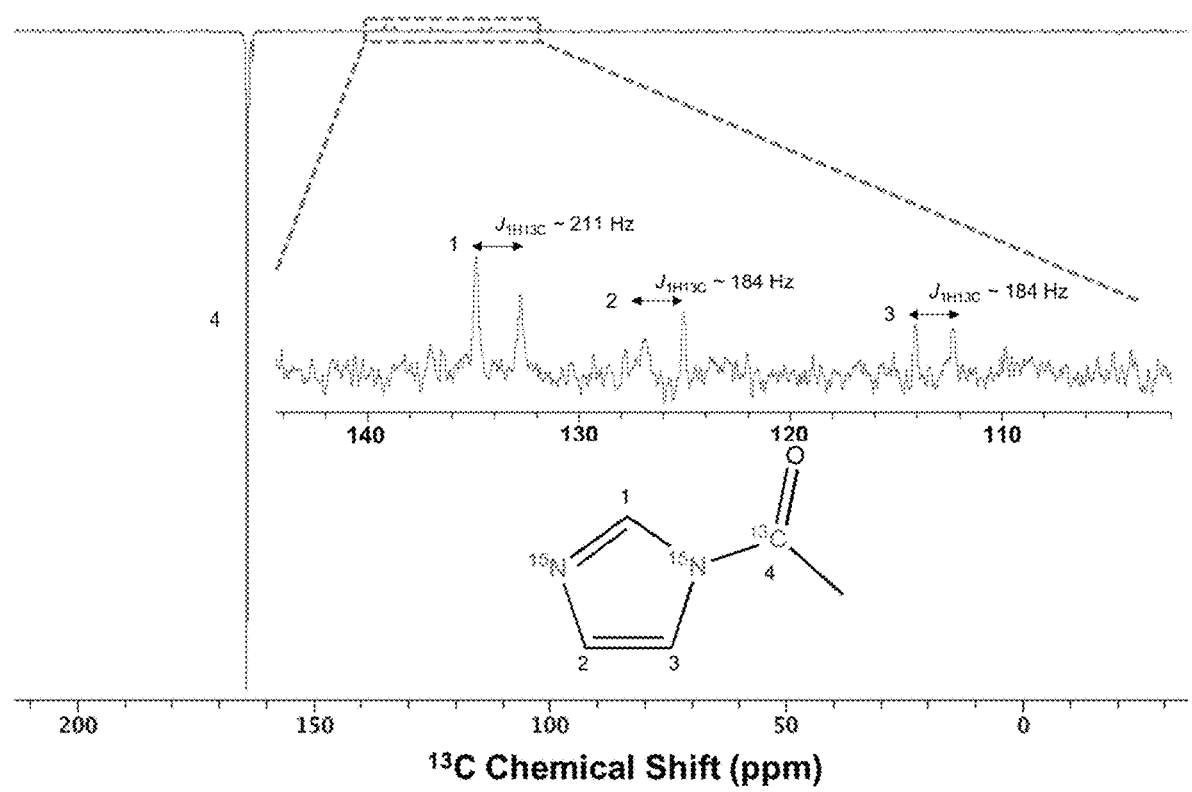
FIG. 9 is an NMR spectrum showing hyperpolarization of $^{13}C$.

One method comprises hyperpolarizing the $^1H$ spins of the cleavable agents via conventional (i.e. milliTesla) SABRE. As an example, $^1H$ hyperpolarization of 1-$^{13}C$-$^{15}N_2$-acetylimidazole is provided in FIG. 2. In this spectrum, $^1H$ SABRE shows relatively weak enhancements while the hydride region shows multiple strong dispersive signals, likely reflecting the lack of symmetry within the ligand field and coupling to $^{15}N$ and $^{13}C$. The clipped signals are from the solvent (in this case, ethanol-d) and the signal at ~4.5 ppm is from ortho-$H_2$. Tentative $^1H$ assignments for the substrate are provided by shift predictions from MNOVA (software available from Mestrelab Research). See also the $^{13}C$ hyperpolarization of 1-$^{13}C$-$^{15}N_2$-acetylimidazole in FIG. 9.

The method of hyperpolarizing the cleavable agent can comprise hyperpolarizing the cleavable agents with NMR-active heteronuclei by (i) driven magnetization transfer from enhanced $^1H$ spins; or (ii) performing SABRE in microTESLA fields (e.g., by using a magnetic shield). The agent spins can also be hyperpolarized at high field such as inside a magnet. The agent can also be created with a network of heteronuclear spins to better facilitate the transfer of magnetization via the scalar coupling network (e.g., "spin relay"), particularly for nuclei that are more distant from the catalyst binding site.

Method of Cleaving the Cleavable Agent

A method of cleaving the cleavable agent is also provided herein. In one method, the cleavable agent's cleavable bond is cleaved by hydrolysis. Such hydrolysis can be initiated with a strong base. In various embodiments, the cleavage of the cleavable agent produces a carboxylic acid or carboxylic acid derivative and a nitrogen-containing heteroaryl structure, such as an imidazole or a pyridinic alcohol. As described above, at least one nitrogen in the nitrogen-containing heteroaryl is isotopically labeled ($^{15}N$) and/or at least one carbon in the carboxylic acid or carboxylic acid derivative is isotopically labeled ($^{13}C$).

The method can also comprise hyperpolarizing the cleavable agent via SABRE within a magnetic shield. Magnetization from $^{15}N$ transfers to $^{13}C$ spins in the more distant carboxylic acid moiety via a "spin-relay" mechanism at low field. Following hyperpolarization of the cleavable agent, the container for the agent is depressurized and rapid cleavage (e.g., rapid hydrolytic cleavage, rapid aminolytic cleavage, or rapid enzymatic cleavage) of the bond between the heteroaryl and carboxylic acid moieties can be performed with a base. The cleavage/activation procedure can also be performed in a stronger magnetic field at which $^{15}N$, $^{13}C$, or other participating nuclear spins undergo slower decay of hyperpolarization (e.g., spin-lattice relaxation ($T_1$) processes), after which the prepared hyperpolarized agent or agents may be transported to the observation field (e.g., the high field of an NMR or MRI magnet) either before or after agent administration to a sample or subject.

Figure 3:
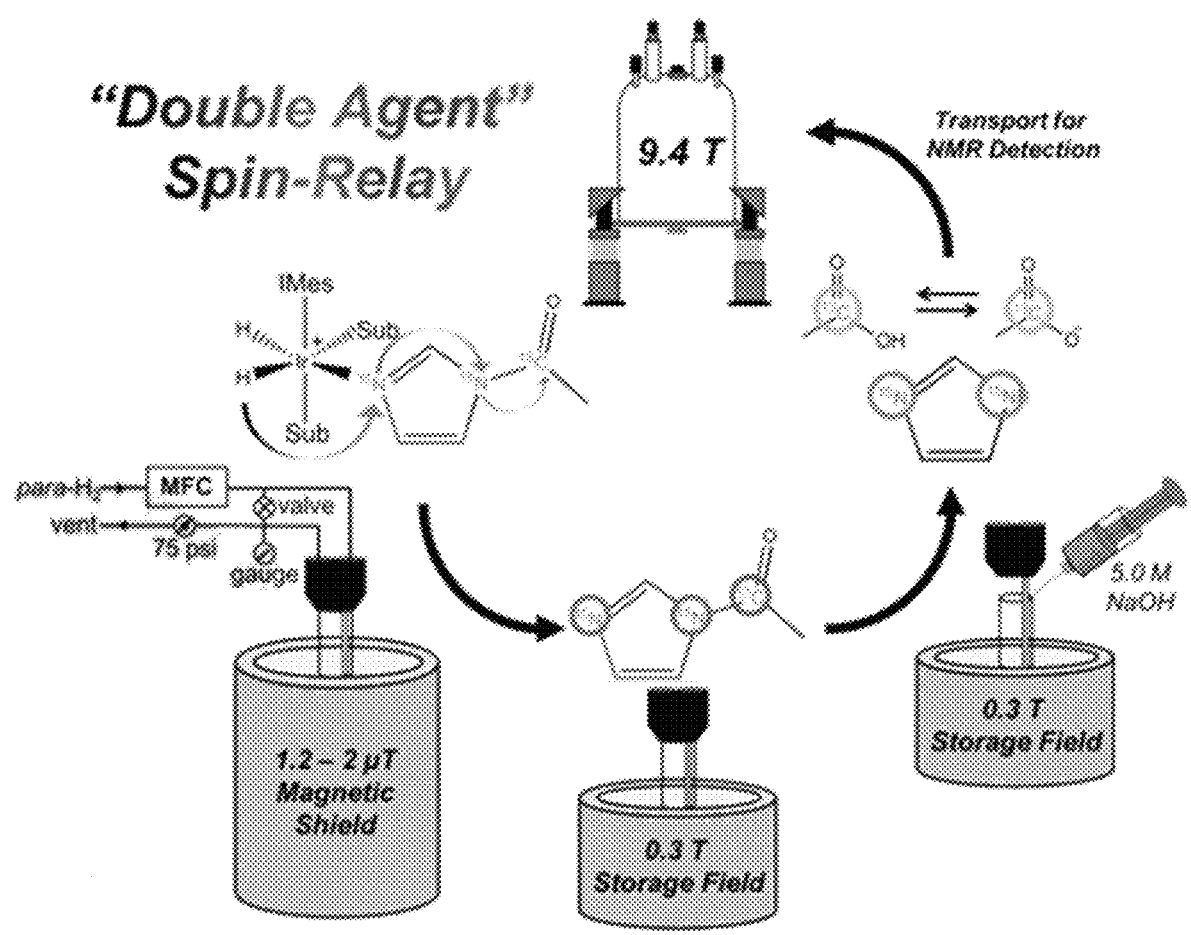
FIG. 3 is a scheme for the production of a hyperpolarized "double agent."

Hyperpolarized carboxylic acid derivatives generated via the SABRE approach are shown in the scheme depicted in FIG. 3. In this approach, the $^{15}N$ spins of an agent (1-$^{13}C$-$^{15}N_2$-acetylimidazole) are hyperpolarized under SABRESHEATH (SABRE in SHield Enables Alignment Transfer to Heteronuclei) conditions with spin-relay of hyperpolarization to distant $^{13}C$ spins. Upon activation (e.g., hydrolytic cleavage of the acetyl group), the hyperpolarized payload is released ($^{13}C$-acetate/acetic acid in the illustrated embodiment). While a variety of Ir-binding moieties can be envisioned, which would be recognized by a skilled person knowledgeable in SABRE catalysts, the illustrated embodiment employs a $^{15}N_2$-imidazole, as it reversibly binds to the Ir catalyst, is biologically relevant (including as a potential pH-imaging agent), and can be functionalized with $^{13}C$-labeled carboxylic acids via cleavable bonds, as described above.

Definitions

The term halo or halogen refers to any radical of fluorine, chlorine, bromine or iodine.

Unless otherwise indicated, an alkyl group as described herein alone or as part of another group is an optionally substituted linear saturated monovalent hydrocarbon substituent containing from one to sixty carbon atoms and preferably one to thirty carbon atoms in the main chain or eight to thirty carbon atoms in the main chain, or an optionally substituted branched saturated monovalent hydrocarbon substituent containing from three to sixty carbon atoms, and preferably eight to thirty carbon atoms in the main chain. Examples of unsubstituted alkyl groups include methyl, ethyl, n-propyl, i-propyl, n-butyl, i-butyl, s-butyl, t-butyl, n-pentyl, i-pentyl, s-pentyl, t-pentyl, and the like. The term alkylene refers to an alkyl group having free valencies on two carbon atoms.

The term alkenyl as employed herein by itself or as part of another group is an optionally substituted linear saturated monovalent hydrocarbon substituent containing from two to sixty carbon atoms and preferably two to thirty carbon atoms in the main chain or eight to thirty carbon atoms in the main chain, or an optionally substituted branched saturated monovalent hydrocarbon substituent containing from three to sixty carbon atoms, and preferably eight to thirty carbon atoms in the main chain, and including at least one double bond between two of the carbon atoms in the chain. Examples of unsubstituted alkenyl groups include ethenyl, 1-propenyl, 2-propenyl, 2-methyl-1-propenyl, 1-butenyl, 2-butenyl, and the like. The term alkenylene refers to an alkenyl group having free valencies on two carbon atoms.

Alkoxy groups are generally alkyl groups described above substituted by an oxygen atom.

The term heteroaryl as used herein alone or as part of another group denotes optionally substituted heterocyclic aromatic groups, preferably monocyclic or bicyclic groups containing from 2 to 12 carbons in the ring portion, such as furanyl, thienyl, pyrrolyl, oxazolyl, thiazolyl, imidazolyl, pyrazolyl, isoxazolyl, isothiazolyl, 1,2,3-oxadiazolyl, 1,2,3-triazolyl, 1,3,4-thiadiazolyl, pyridinyl, pyridazinyl, pyrimidinyl, 1,3,5-triazinyl, and the like.

The term "substituted" as in "substituted alkyl," and the like, means that in the group in question (i.e., the alkyl, aryl or other group that follows the term), at least one hydrogen atom bound to a carbon atom is replaced with one or more substituent groups such as hydroxy (—OH), alkylthio, phosphino, amido (—CON($R_A$)($R_B$)), wherein $R_A$ and $R_B$ are independently hydrogen, alkyl, or aryl), amino (—N($R_A$)($R_B$)), wherein $R_A$ and $R_B$ are independently hydrogen, alkyl, or aryl), halo (fluoro, chloro, bromo, or iodo), silyl, nitro (—$NO_2$), an ether (—$OR_A$ wherein $R_A$ is alkyl or aryl), an ester (—OC(O)$R_A$ wherein $R_A$ is alkyl or aryl), keto (—C(O)$R_A$ wherein $R_A$ is alkyl or aryl), heterocyclo, and the like. When the term "substituted" introduces a list of possible substituted groups, it is intended that the term apply to every member of that group. That is, the phrase "optionally substituted alkyl or aryl" is to be interpreted as "optionally substituted alkyl or optionally substituted aryl."

Having described the invention in detail, it will be apparent that modifications and variations are possible without departing from the scope of the invention defined in the appended claims.

EXAMPLES

The following non-limiting examples are provided to further illustrate the present invention:

Example 1: Synthesis of 1-$^{13}C$-$^{15}N_2$-acetylimidazole

1-$^{13}C$-$^{15}N_2$-acetylimidazole was synthesized as shown in Scheme 1, below:

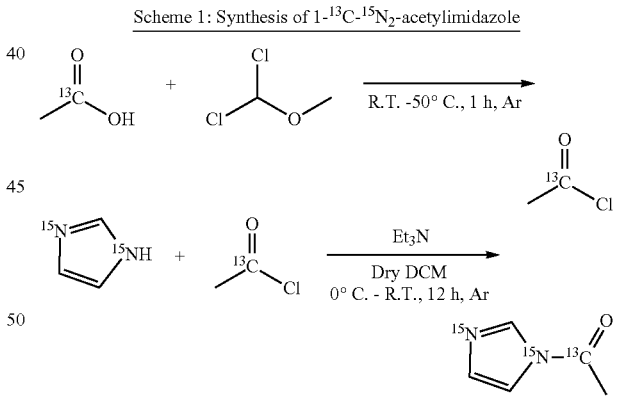

1-$^{13}C$-Acetic acid (0.890 ml, 15.5 mmol) and α,α-dichloromethyl methyl ether (1.410 ml, 15.5 mmol) were added to a 100-ml $R_B$ flask equipped with a stir bar. The reaction was allowed to proceed from room temperature to 50° C. for 1 h under argon atmosphere. The resulting yellow crude oil was then chilled in an ice bath for several minutes before dropwise addition of $^{15}N_2$-imidazole (1.00 g, 14.3 mmol) previously dissolved in dry dichloromethane. A precipitate was immediately formed and the reaction was allowed to stir for an additional 30 min before addition of triethylamine (2.20 ml, 15.5 mmol). The reaction was allowed to stir overnight before addition of diethyl ether (100 ml). The addition of diethyl ether caused precipitation of the triethylamine hydrochloride salt, later to be removed via filtration. The filtrate was then evaporated using a rotovap and solid product was collected. The product was recrystallized three times using a DCM:hexane (50:50) mixture. Pure 1-$^{13}$C-$^{15}$N$_2$-acetylimidazole crystals were then dried and collected, yielding 1.37 g (85%).

The experiment was performed with 20 mM methanol-d4 solutions of $^{15}$N$_2$,$^{13}$C-acetylimidazole, 1 mM Ir-catalyst precursor [IrCl—(COD)(IMes)] (where IMes=1,3-bis(2,4,6-trimethylphenyl)-imidazol-2-ylidene and COD=cyclooctadiene), and ~75-85% parahydrogen enrichment (at 75 psi) with a flow rate of 80 sccm provided by a home-built para-H$_2$ generator. The catalyst is activated via para-H$_2$ bubbling in the presence of substrate for at least ~30 mins prior to SABRE hyperpolarization experiments. SABRE-SHEATH mixing fields of 2 µT ($^{13}$C) and 1.2 µT ($^{15}$N) were used for pre- and post-cleaving experiments, which were performed at room temperature prior to NMR acquisition with a 400 MHz Bruker AVANCE III spectrometer.

Example 2: Synthesis of 1-$^{13}$C-$^{15}$N$_2$-pyruvyl-imidazole

1-$^{13}$C-$^{15}$N$_2$-pyruvyl-imidazole was synthesized as shown in Scheme 2, below:

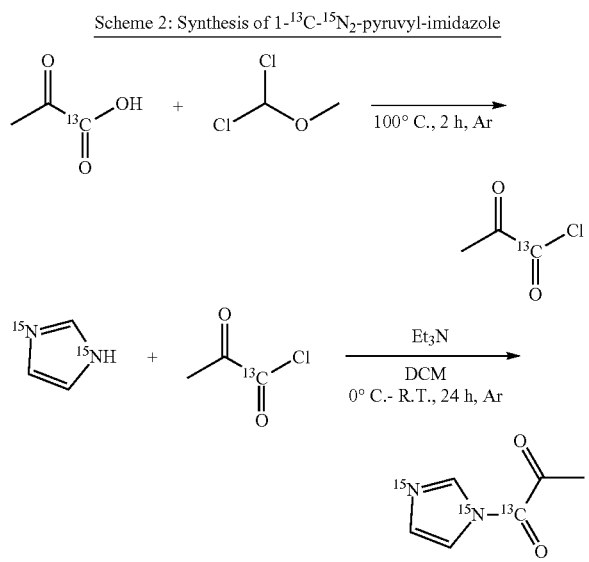

Scheme 2: Synthesis of 1-$^{13}$C-$^{15}$N$_2$-pyruvyl-imidazole 2-oxopropionic acid and α,α-dichloromethyl methyl ether were added to a 100-ml RB flask equipped with a stir bar. The reaction was occurred at 100° C. for 2 h under argon atmosphere. The resulting yellow crude oil was then chilled in an ice bath for several minutes before dropwise addition of $^{15}$N$_2$-imidazole previously dissolved in dichloromethane. A precipitate was immediately formed and the reaction was allowed to stir for an additional 30 min before addition of triethylamine. The reaction was allowed to stir for 24 h before addition of diethyl ether. The addition of diethyl ether caused precipitation of the triethylamine hydrochloride salt, later to be removed via filtration. The filtrate was then evaporated using a rotovap and solid product was collected. The product was recrystallized three times using a DCM:hexane (50:50) mixture. Pure 1-$^{13}$C-$^{15}$N$_2$-acetylimidazole crystals were then dried and collected, yielding 1.37 g (85%).

Example 3: Calculation of SABRE Enhancements $^1$H SABRE and $^{13}$C/$^{15}$N SABRE-SHEATH enhancements were calculated using the following equation:

$$\varepsilon = \left(\frac{S_{HP}}{S_{REF}}\right) \times \left(\frac{[REF]}{[HP]}\right) \times \left(\frac{A_{REF}}{A_{HP}}\right),$$

where ε is the calculated enhancement, $S_{HP}$ is the absolute integral of the hyperpolarized signal, $S_{REF}$ is the absolute integral of the signal from a thermally-polarized reference species (here, acquired with a 300 s relaxation delay time), [REF] is the concentration of the reference species, [HP] is the concentration of the hyperpolarized species, $A_{REF}$ is the cross-sectional area of the NMR tube containing the reference species, and $A_{HP}$ is the cross-sectional area of the hyperpolarized sample NMR tube (in the present work, $A_{REF}/A_{HP}=1.12$).

Figure 4:
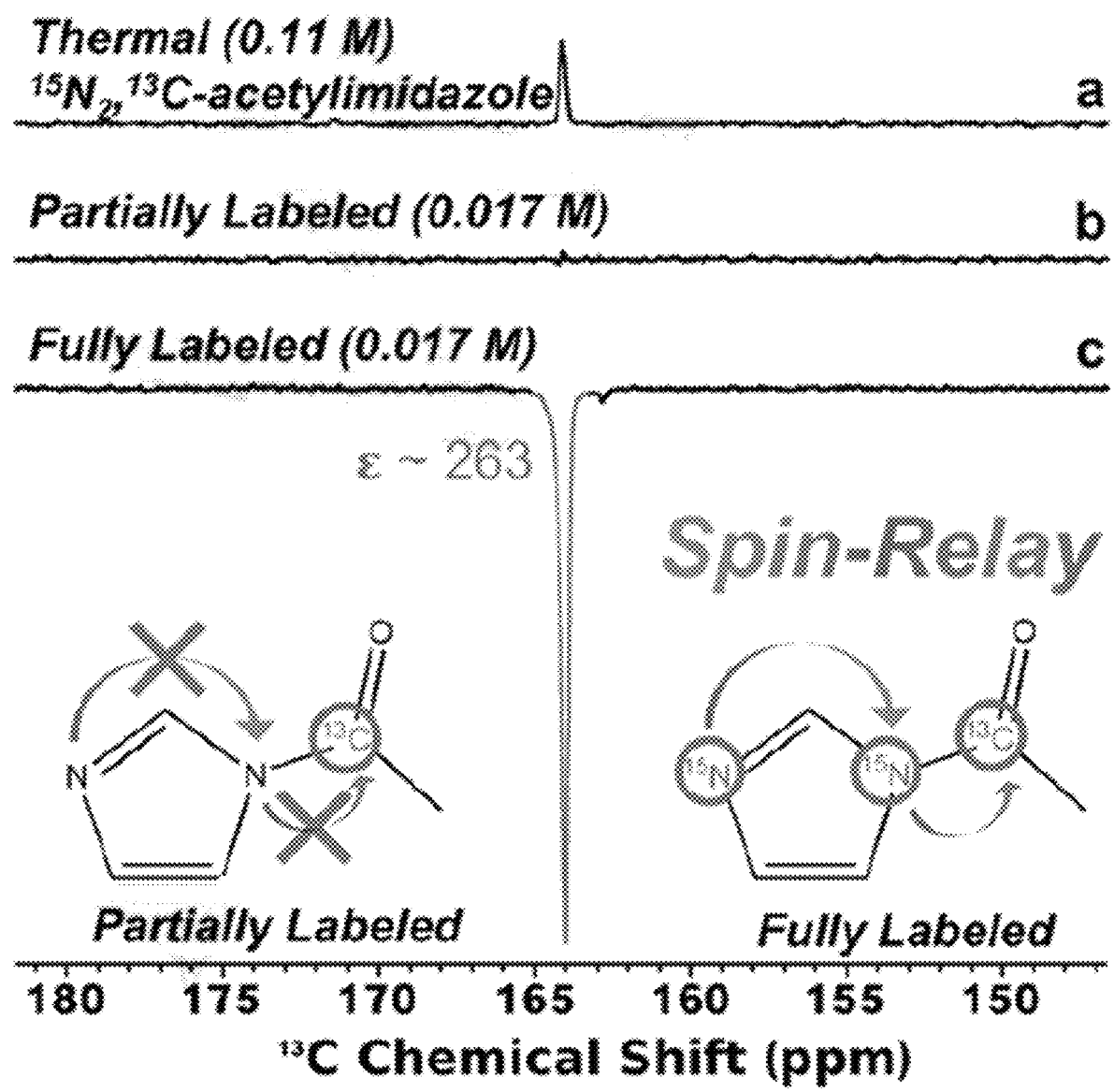
FIG. 4 is an NMR spectrum depicting the $^{13}C$ shift as described in Example 3.

When SABRE-SHEATH was attempted with only a partially labeled construct (20 mM 1-$^{13}$C-acetylimidazole, without $^{15}$N-labeling), minimal polarization transfer to the distant $^{13}$C-labeled acetyl moiety was observed (FIG. 4b). However, use of fully-labeled construct (with $^{15}$N labeling) yielded significant, ~263-fold $^{13}$C enhancements of the carbonyl in 1-$^{13}$C-$^{15}$N$_2$-acetylimidazole (FIG. 4c) when compared to a reference signal (0.11 M thermally polarized 1-$^{13}$C-$^{15}$N$_2$-acetylimidazole; FIG. 4a). These results support the conclusion that the distant $^{13}$C of the acetyl moiety is hyperpolarized through a spin-relay mechanism, wherein $^{15}$N of imidazole is first hyperpolarized within the sub-micro-Tesla field, and transfers polarization to the acetyl $^{13}$C through the heteronuclear J-coupling network (FIG. 3).

Figure 2:
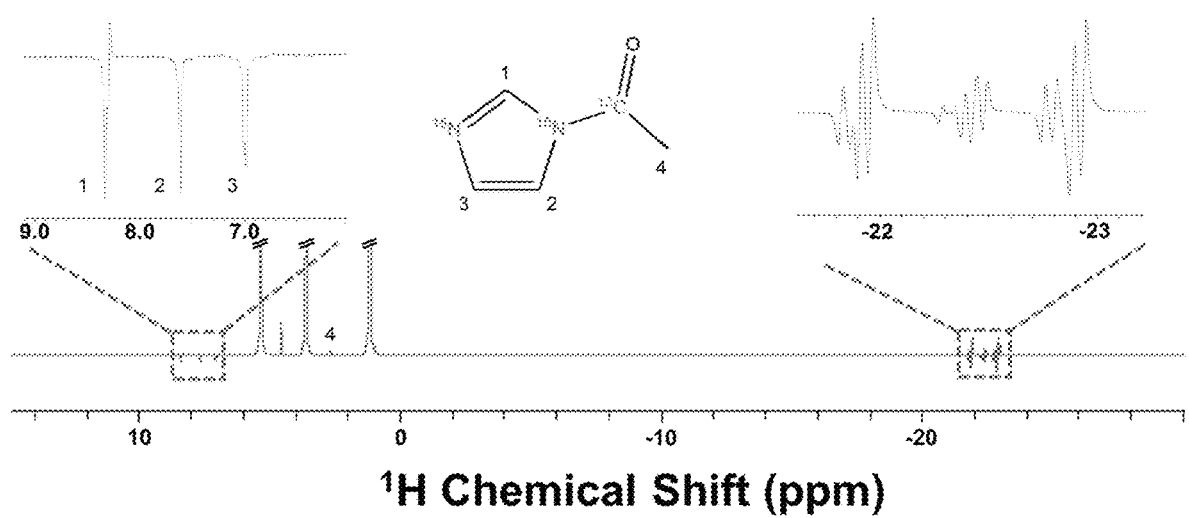
FIG. 2 is an example of $^1$H hyperpolarization of 1-$^{13}$C-$^{15}$N$_2$-acetylimidazole (of type B).
Figure 5:
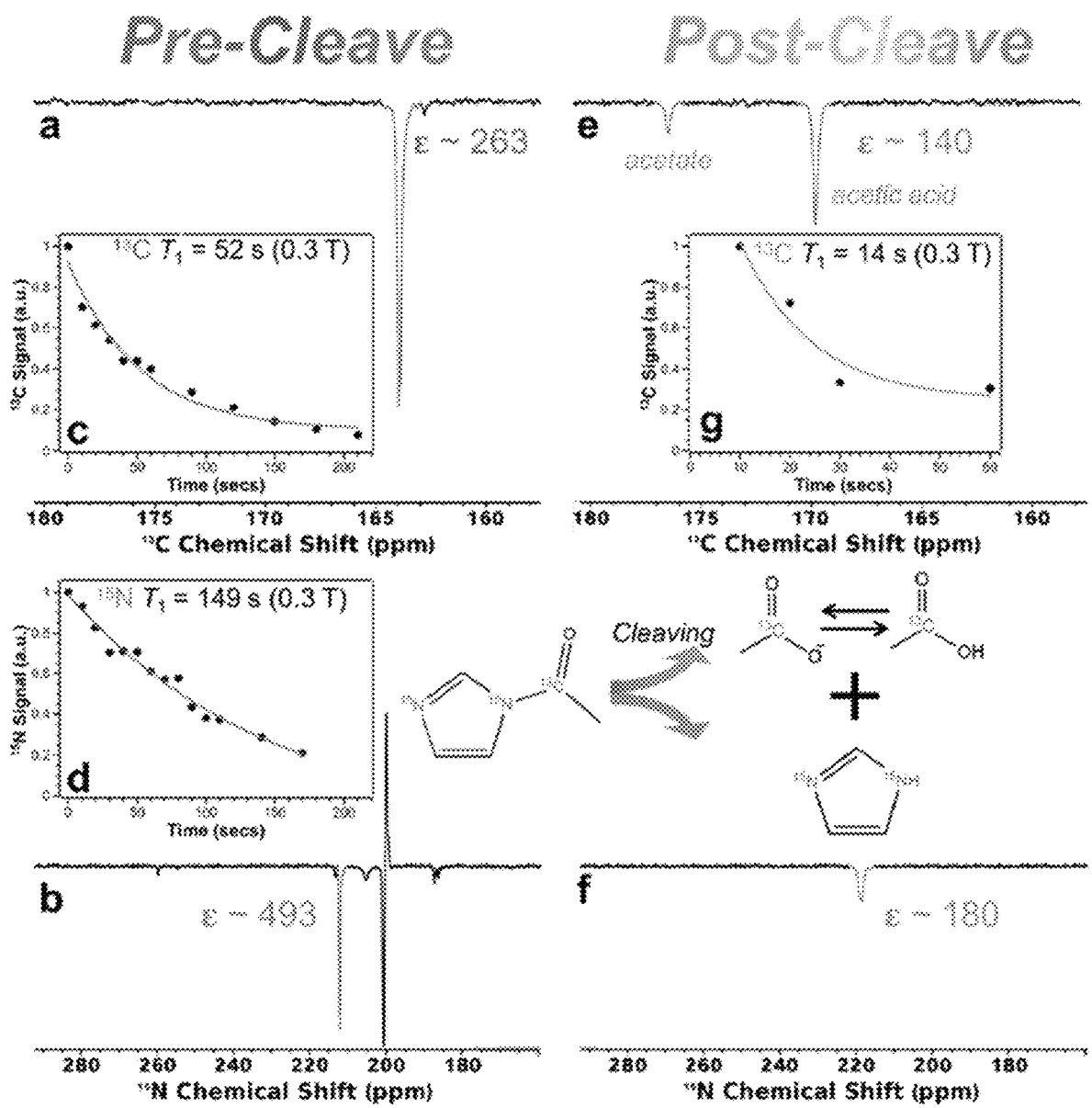
FIG. 5 is NMR spectra depicting both $^{13}C$ and $^{15}N$ shifts as described in Example 3.
Figure 6:
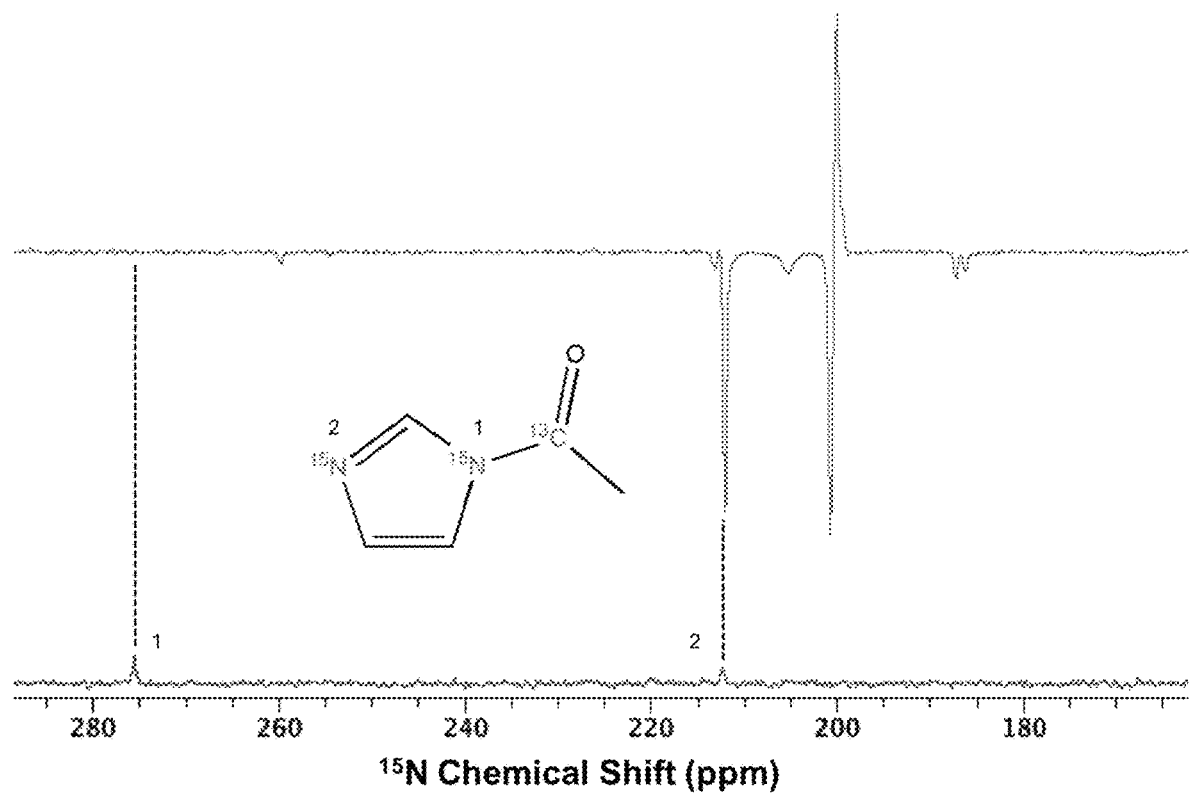
FIG. 6 is an NMR spectrum showing $^{15}N$ hyperpolarized and thermally polarized signals.

Heteronuclear hyperpolarization of 1-$^{13}$C-$^{15}$N$_2$-acetylimidazole also resulted in $^{15}$N enhancements ~493 for free 1-$^{13}$C-$^{15}$N$_2$-acetylimidazole (unbound to the catalyst; FIG. 5b). HP signals were also observed from naturally abundant $^{13}$C spins of the imidazole ring with enhancements of ~100. Interestingly, the HP $^{15}$N spectrum (FIG. 5b) also shows hyperpolarization of a signal from Ir-bound species that appears stronger than that of the $^{15}$N signals from unbound substrate at ~275 ppm and ~212 ppm (see also FIG. 6; note that the concentration of catalyst-bound species will be an order of magnitude lower than that of the free substrate). Moreover, only one HP resonance attributed to unbound substrate is observed (~212 ppm). It is noteworthy that high-field 15N enhancements of structurally similar substrates show similar behavior to the present SABRESHEATH results, wherein bound substrates can show strong dispersive HP signals. Thus, it is possible that the substrate may be hyperpolarized at high field upon transfer for NMR detection due to residual p-H$_2$ in solution. Additionally, the anticipated inequivalence of the bound sites would be expected to result in one unbound signal and three bound signals for each $^{15}$N, potentially giving a total of eight unique signals (neglecting any significant J splittings). Such complexity is also reflected in the $^1$H SABRE hydride region (FIG. 2).

After polarization transfer to $^{13}$C and $^{15}$N in the µT magnetic shield, the solution was transferred to a 0.3 T storage field, where heteronuclear relaxation times can be relatively long. T1 decay constants were measured by repeating the hyperpolarization cycle with variable delay periods at 0.3 T prior to rapid transfer to 9.4 T for detection. The resulting $^{13}$C and $^{15}$N T1's were 52±8 s and 149±42 s, respectively, at 0.3 T-indicating sufficient time not only for agent administration, but additional preparation steps as well (as described below).

Figure 7:
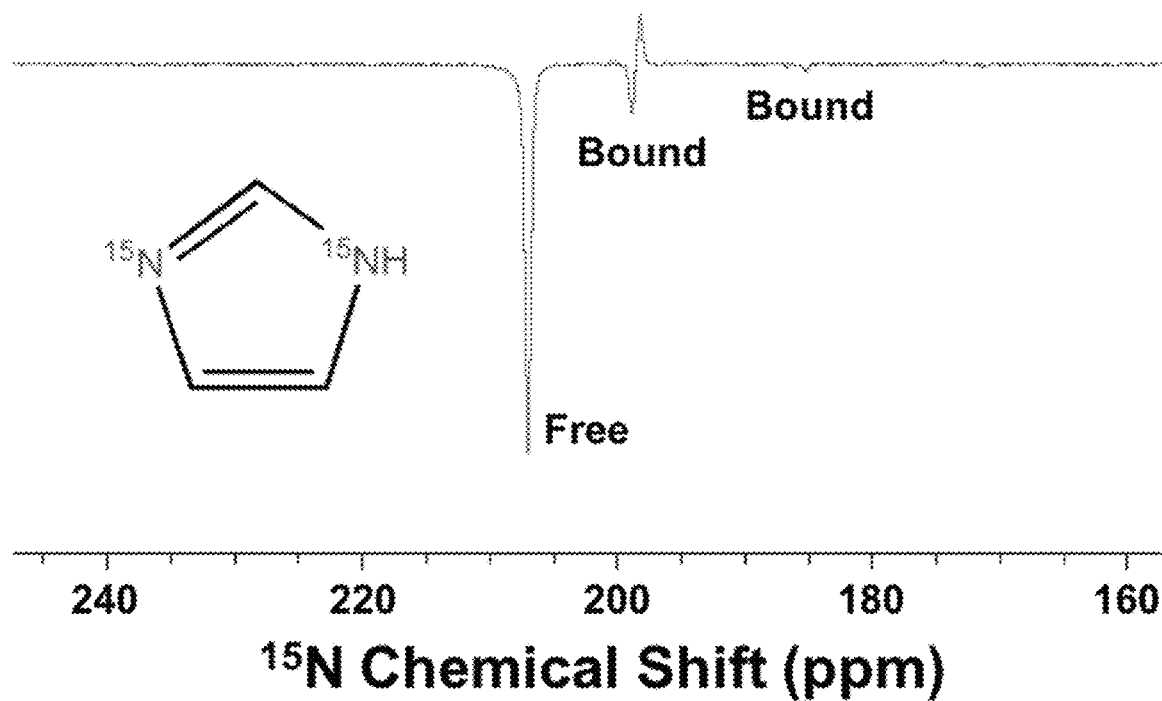
FIG. 7 is an NMR spectrum showing the re-hyperpolarization of $^{15}N$ of nascent imidazole.

Following spin-relay of SABRE hyperpolarization to $^{13}$C spins of 1-$^{13}$C-$^{15}$N$_2$-acetylimidazole, we immediately transferred the solution to 0.3 T, depressurized it to 1 atm, added ~200 μL of 5.0 M NaOH to hydrolytically cleave the acetyl moiety, and transferred the sample to 9.4 T for detection. FIG. 5e and FIG. 5f respectively show retention of $^{13}$C and $^{15}$N hyperpolarization post-hydrolysis with rapid and complete conversion to HP $^{13}$C-acetate/acetic acid and $^{15}$N-imidazole occurring within the timescale of base addition and sample transfer-supported by corresponding changes to the $^{13}$C and $^{15}$N chemical shifts (compare with the precleavage HP $^{13}$C spectrum, repeated in FIG. 5a). Free acetate/acetic acid and imidazole exhibit $^{13}$C and $^{15}$N enhancements of ~139 and ~180, respectively. The single enhancement value reported for acetate/acetic acid resonances is an average that assumes similar $^{13}$C T1 losses during the preparation period. An estimate of that relaxation rate can be obtained by repeating the SABRE-SHEATH hyperpolarization and cleavage steps with fresh (i.e. intact) substrate, followed by variable delay at 0.3 T prior to high-field detection. The corresponding decay curve (FIG. 5g) gives a T1 value of ~14±9 s at 0.3 T for the combined $^{13}$C signal. The value calculated here for imidazole $^{15}$N enhancement includes the fact that magnetization achieved on one substrate $^{15}$N spin becomes effectively "diluted" by a factor of two (because the two $^{15}$N spins are magnetically equivalent). It should also be noted that the lower enhancements for acetate/acetic acid and imidazole are consistent with the expected T1 losses during the ~10 s elapsed time of the hydrolysis procedure; moreover, dilution from base addition is not accounted for in the reported enhancement. Thus, minimal hyperpolarization loss results from the cleavage process itself or the brief exposure of the sample to paramagnetic O$_2$ from air. Importantly, while $^{15}$N spins of free imidazole can be "re-hyperpolarized" by repeating the SABRE-SHEATH procedure (FIG. 7), any attempt to re-hyperpolarize free acetic acid or acetate post-cleaving yields no $^{13}$C enhancement (FIG. 8)—further indicating the importance of the spin relay within the intact substrate for achieving $^{13}$C-acetic acid/acetate hyperpolarization.

Example 4: Calculations of Signal Enhancements

Figure 8:
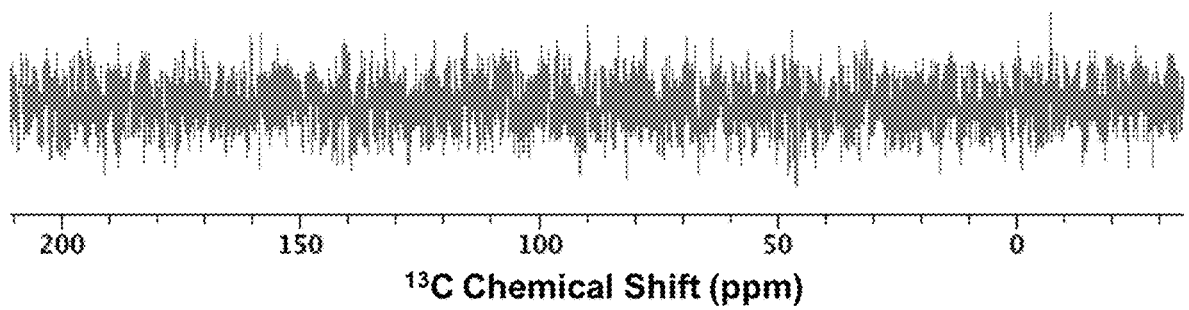
FIG. 8 is an NMR spectrum showing an attempt to re-hyperpolarize $^{13}C$.

Table 1 and Table 2 show calculations of $^{13}$C signal enhancement for FIG. 8 and FIG. 2, respectively. For Table 2, the integral post-cleave $^{15}$N-free species shown was obtained after dividing the measured integral by 2, reflecting the presence of two magnetically equivalent $^{15}$N spins in $^{15}$N$_2$-imidazole. Concentrations for post-cleave species were not corrected for dilution (during the hydrolysis process), so true polarization enhancements were likely up to ~30% larger than those reported herein.

TABLE 1

Calculations of $^{13}$C signal enhancement for FIG. 8

| | Fully Labelled $^{13}$C-Free |
|---|---|
| S$_{REF}$ | 481900.15 |
| S$_{HP}$ | 17519238.15 |
| [REF] | 110 mM |
| [HP] | 17 mM |
| ε | 263 |

TABLE 2

Calculations of $^{13}$C and $^{15}$N signal enhancements for FIG. 2

| | Pre-Cleave $^{13}$C-Free | Pre-Cleave $^{15}$N-Free |
|---|---|---|
| S$_{REF}$ | 481900.15 | 26677.48 |
| S$_{HP}$ | 17519238.15 | 1813482.01 |
| [REF] | 110 mM | 110 mM |
| [HP] | 17 mM | 17 mM |
| ε | 263 | 493 |

| | Post-Cleave $^{13}$C-Free | Post-Cleave $^{15}$N-Free |
|---|---|---|
| S$_{REF}$ | 481900.15 | 26677.48 |
| S$_{HP}$ | 9275396.76 | 664183.75 |
| [REF] | 110 mM | 110 mM |
| [HP] | 17 mM | 17 mM (34 mM in $^{15}$N) |
| E | 139 | 180 |

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above compounds and methods without departing from the scope of the invention, it is intended that all matter contained in the above description and shown in the accompanying drawings shall be interpreted as illustrative and not in a limiting sense.

The invention claimed is:

1. A cleavable agent selected from the group consisting of 1-$^{13}$C-$^{15}$N$_2$-acetylimidazole and 1-$^{13}$C-$^{15}$N$_2$-pyruvyl-imidazole.

* * * * *